(12) United States Patent
Kai et al.

(10) Patent No.: US 6,464,977 B2
(45) Date of Patent: Oct. 15, 2002

(54) SOLID PREPARATION FOR DIALYSIS AND PROCESS FOR PRODUCING THE SAME

(75) Inventors: Toshiya Kai, Osaka (JP); Kazuyuki Yamamoto, Osaki (JP); Kazutaka Fujiki, Osaka (JP); Makoto Sato, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/963,550

(22) Filed: Sep. 27, 2001

(65) Prior Publication Data

US 2002/0061334 A1 May 23, 2002

(30) Foreign Application Priority Data

Sep. 27, 2000 (JP) ........................................ 2000-293330

(51) Int. Cl.7 ............................................. A61K 39/395
(52) U.S. Cl. ..................... 424/153; 424/1.29; 424/717; 424/210
(58) Field of Search ................................ 424/717, 210, 424/1.29, 153

(56) References Cited

U.S. PATENT DOCUMENTS

| | | | |
|---|---|---|---|
| 4,489,535 A | * | 12/1984 | Veltman ........................ 53/431 |
| 4,756,838 A | * | 7/1988 | Veltman ........................ 252/1 |
| 5,540,842 A | | 7/1996 | Aoyama et al. ............ 210/647 |

FOREIGN PATENT DOCUMENTS

| | | |
|---|---|---|
| EP | 0 417 478 A1 | 3/1991 |
| EP | 0 602 921 A1 | 6/1994 |
| WO | 92/16117 A1 | 10/1992 |

OTHER PUBLICATIONS

Database WPI, Section Ch, Week 200003, Derwent Publications Ltd., London, GB; AN 1997–175602, XP002187032, JP 02 987488 B (Tomita Seiyaku KK), Dec. 6, 1999.

* cited by examiner

Primary Examiner—Jose' G. Dees
Assistant Examiner—Robert M Dewitty
(74) Attorney, Agent, or Firm—Kubovcik & Kubovcik

(57) ABSTRACT

A solid preparation for dialysis for preparing a double preparation type sodium bicarbonate solid preparation for dialysis in which there is no fear that a sugar is decomposed or colored, and which can maintain stability and also is excellent in content homogeneity and a process for producing the same. The solid preparation for dialysis is a mixture of a first composition composed of core particles including sodium chloride that are coated with a coating layer containing one or more electrolytes, a second composition composed of core particles including a sugar that are covered with a coating layer containing one or more electrolytes, and an acid.

8 Claims, No Drawings

SOLID PREPARATION FOR DIALYSIS AND PROCESS FOR PRODUCING THE SAME

FIELD OF THE INVENTION

The present invention relates to a solid preparation for dialysis for use in preparing a dialysate containing sodium bicarbonate. That is, the present invention relates to a solid preparation containing electrolytes, an acid and a sugar, which is to be used in sodium bicarbonate solid preparations for dialysis which usually comprise two preparations. These are a preparation containing sodium bicarbonate in addition to a preparation containing electrolytes, an acid, and a sugar and not containing sodium bicarbonate (hereinafter referred to as a double preparation type sodium bicarbonate solid preparation for dialysis).

BACKGROUND OF THE INVENTION

When hemodialysis is carried out for a patient having decreased kidney function, the blood of the patient is purified in an artificial kidney. A dialysate is perfused inside of this artificial kidney, and waste products in the blood are generally transferred into the dialysate through a dialysis membrane. As this dialysate, acetic acid-containing dialysate has widely been used. In recent years, however, it has been substituted by a dialysate using sodium bicarbonate that remarkably reduces discomfort during the hemodialysis.

The dialysate containing sodium bicarbonate is usually prepared from two kinds of dialysate preparations, one being a liquid preparation containing electrolyte components (for example, sodium chloride, potassium chloride, calcium chloride, magnesium chloride, and sodium acetate) and a pH adjusting agent (for example, acetic acid) (hereinafter referred to as liquid A preparation), and the other being a liquid preparation containing sodium bicarbonate (hereinafter referred to as liquid B preparation). The dialysate preparations sometimes contain a sugar such as glucose, or another preparation containing a sugar is mixed with these dialysate preparations.

The liquid A preparation and the liquid B preparation have hitherto been sold in the form of dense liquids prepared at a predetermined concentration, and users have diluted them with water for use. However, since about 300 liters of a dialysate is needed for one patient for one dialysis, in the case of conducting dialysis treatments for many patients, a large quantity of a dense liquid is used, and dilution of it with water is needed. Thus, in order to relieve a burden on people who prepare a dialysate, and to save space, cases using a B preparation that is pulverized have increased. A double preparation type sodium bicarbonate solid preparation for dialysis in which the A preparation is also pulverized has also been recently developed.

As a pulverized double preparation type sodium bicarbonate solid preparation for dialysis, a preparation for dialysis that comprises two compositions, that is, one powdery preparation (A preparation) comprising electrolytes (except for sodium bicarbonate), glucose and a liquid acid, and another powdery preparation (B preparation) comprising only sodium bicarbonate, or sodium bicarbonate and sodium acetate or glucose, has been disclosed (Japanese Patent Publication No. 2749375 and No. 2751933, and Japanese Patent Unexamined Publication No. Hei 3-38527).

Among these preparations for dialysis, either a dry method or a fluidized bed method is used to produce the A preparation. The dry method comprises stirring and mixing electrolytes except for sodium bicarbonate and glucose using a stirring mixer, subsequently pulverizing the mixture using a pulverizer, after that mixing the mixture again, and after granulating the mixture using a dry granulator, mixing the granulated mixture with a liquid acid. Moreover, the fluidized bed method comprises mixing sodium chloride and glucose using a stirring mixer, and, after granulating the mixture while spraying the mixture in a fluidized bed granulator with an aqueous solution obtained by dissolving electrolytes except for sodium chloride and sodium bicarbonate into water, mixing them with a liquid acid.

However, in a preparation for dialysis that is obtained by the methods described above, glucose is likely to be decomposed or colored because time for heating glucose during the production process is long. Thus it has been generally considered that a double preparation type sodium bicarbonate solid preparation for dialysis in which the A preparation contains glucose has a shortened period of time for maintaining stability as compared with a sodium bicarbonate solid preparation for dialysis comprising three preparations where glucose is separately provided. Furthermore, it is difficult to achieve content homogeneity in a double preparation type sodium bicarbonate solid preparation for dialysis that is obtained by the methods described above.

SUMMARY OF THE INVENTION

In view of the above circumstances, it is an object of the present invention to provide a solid preparation for dialysis containing electrolytes (except for sodium bicarbonate), an acid and a sugar. The preparation can maintain stability equal to a sodium bicarbonate solid preparation for dialysis comprising three preparations where a sugar is separately provided, is excellent in content homogeneity and there is no fear that the sugar is decomposed or colored.

In order to solve the above problems, the present inventors wholeheartedly investigated. They found out that the desired object can be achieved by granulating a composition containing electrolytes except for sodium bicarbonate and a composition containing a sugar separately and subsequently mixing them with an acid to produce an A preparation of a double preparation type sodium bicarbonate solid preparation for dialysis, and attained the present invention.

That is, the present invention is a solid preparation for dialysis comprising a mixture of particles of a first composition containing one or more electrolytes selected from the group consisting of sodium chloride, calcium chloride, magnesium chloride, potassium chloride and sodium acetate, particles of a second composition containing a sugar and one or more electrolytes selected from the group consisting of sodium chloride, calcium chloride, magnesium chloride, potassium chloride and sodium acetate, and an acid.

Further, the present invention is a process for producing a solid preparation for dialysis comprising the following steps (1) to (3):

(1) a step of spraying an aqueous solution containing one or more electrolytes selected from the group consisting of calcium chloride, magnesium chloride, potassium chloride and sodium acetate onto core particles containing sodium chloride, and drying the coated particles to obtain a first composition;

(2) a step of spraying an aqueous solution containing one or more electrolytes selected from the group consisting of sodium chloride, calcium chloride, magnesium chloride, potassium chloride and sodium acetate onto core particles containing a sugar, and drying the coated particles to obtain a second composition; and (3) a step of mixing the first composition obtained in step (1) and the second composition obtained in step (2), and further mixing them with an acid to obtain the solid preparation for dialysis.

Moreover, the present invention is a process for producing a solid preparation for dialysis comprising the following steps (1) to (3):

(1) a step of spraying an aqueous solution containing one or more electrolytes selected from the group consisting of calcium chloride, magnesium chloride, potassium chloride and sodium acetate onto core particles containing sodium chloride, and drying the coated particles to obtain a first composition;

(2) a step of spraying an aqueous solution containing one or more electrolytes selected from the group consisting of sodium chloride, calcium chloride, magnesium chloride, potassium chloride and sodium acetate onto core particles containing a sugar, and drying the coated particles to obtain a second composition; and (3) a step of mixing an acid with the first composition obtained in step (1), and subsequently mixing the resultant mixture with the second composition obtained in step (2) to obtain the solid preparation for dialysis.

DETAILED DESCRIPTION OF THE INVENTION

The first composition of the solid preparation for dialysis preferably has a characteristic feature that core particles containing sodium chloride are covered with a coating layer containing one or more electrolytes selected from the group consisting of calcium chloride, magnesium chloride, potassium chloride and sodium acetate.

Moreover, the second composition of the solid preparation for dialysis preferably has a characteristic feature that core particles containing a sugar are covered with a coating layer containing one or more electrolytes selected from the group consisting of sodium chloride, calcium chloride, magnesium chloride, potassium chloride and sodium acetate.

Sodium chloride of the core particles forming the first composition may be any one as long as it is in the solid state and forms core particles, and sodium chloride having a particle diameter of about 75 to 1,700 $\mu$m and which is in a crystalline state is preferable.

The core particles may include particles of an electrolyte such as magnesium chloride, calcium chloride, potassium chloride, sodium acetate or the like in addition to sodium chloride. The content of the electrolyte particles in the core particles is at most 15% by weight. On producing the first composition of the present invention, the electrolyte may be used as it is without being pulverized. Also, in advance, the electrolyte may be pulverized into particles having a particle diameter of 75 to 1,700 $\mu$m by a pulverizer or a particle size selector, or may be granulated into granules having a similar size by wet or dry granulation.

The coating layer of the particles forming the above first composition contains one or more electrolytes selected from the group consisting of calcium chloride, magnesium chloride, potassium chloride and sodium acetate. Moreover, the electrolytes may contain sodium chloride in addition to the above components. The content of sodium chloride included in the coating layer is at most 50% by weight.

As the calcium chloride, calcium chloride dihydrate, calcium chloride monohydrate, calcium chloride anhydride or the like is used. As the magnesium chloride, magnesium chloride hexahydrate or the like is preferably used. As the sodium acetate, sodium acetate anhydride, sodium acetate trihydrate or the like is preferably used.

The electrolytes contained in the coating layer of the first composition are used to form a coating layer on the core particles by dissolving the electrolytes in water to prepare an aqueous solution, spraying the solution onto the core particles of the first composition, and drying the particles. The concentration of the electrolytes in the aqueous solution is preferably 15 to 50% by weight and more preferably 25 to 40% by weight. If the concentration of the aqueous solution is lower than 15% by weight, it takes a longer time to coat the core particles since the quantity of the aqueous solution becomes greater. If the concentration of the aqueous solution is higher than 50% by weight, the electrolytes are not fully dissolved into the water and there is a fear that a suspension will be formed.

As the sugar of the core particles forming the above second composition, glucose, maltose, xylitol, trehalose or the like is used. Glucose is preferably used. The sugar is preferably a powder having a particle diameter of about 45 to 1,700 $\mu$m.

The core particles may include particles of an electrolyte such as sodium chloride, magnesium chloride, calcium chloride, potassium chloride, sodium acetate or the like in addition to the sugar component. The content of the particles of electrolyte in the core particles is at most 50% by weight. On producing the second composition of the present invention, the electrolyte may be used as it is without being pulverized. Moreover, in advance, the electrolyte may be pulverized into particles having a particle diameter of 75 to 1,700 $\mu$m by a pulverizer or a particle size selector, or may be granulated into granules having a similar size by wet or dry granulation.

The coating layer of the particles forming the above second composition contains one or more electrolytes selected from the group consisting of sodium chloride, calcium chloride, magnesium chloride, potassium chloride and sodium acetate. The electrolytes are used to form a coating layer on the core particles by dissolving the electrolytes into water to prepare an aqueous solution, spraying the solution onto the core particles containing the sugar component, and drying the particles. The concentration of the sugar component in the aqueous solution is preferably 1 to 60% by weight, and more preferably 15 to 40% by weight. Moreover, the coating layer may contain glucose in addition to the electrolytes. The content of the glucose in the coating layer is at most 50% by weight.

The first composition and the second composition of the solid preparation for dialysis of the present invention can be obtained by granulation according to a centrifugal fluidized bed granulation method, a fluidized bed granulation method, an agitating fluidized bed granulation method or the like. For both the first composition and the second composition, an agitating fluidized bed granulation method is preferably used. The first composition and the second composition are granulated by the above granulation methods into granules having an average particle diameter of 300 to 1,700 $\mu$m. By this process, the first composition and the second composition can be mixed homogeneously, and a solid preparation for dialysis that is excellent in homogeneity can be obtained.

An agitating fluidized bed granulation apparatus is used for the agitating fluidized bed granulation method. The agitating fluidized bed granulation apparatus is an apparatus in which the core particles are agitated and fluidized by a fluidizing action of an airflow from the vicinity of the wall and an agitating action by rotation of a rotator in the bottom of the apparatus, and an aqueous solution containing a component forming the coating layer is sprayed to form a homogeneous coating layer on the core particles.

The flow rate of the airflow is preferably 0.2 to 300 m³/min, more preferably, 0.5 to 200 m³/min. If the flow rate is less than 0.2 m³/min, the core particles are likely to form aggregates with one another. Moreover, if the flow rate is greater than 300 m³/min, the components in the aqueous solution are apt to cause a spray dry phenomenon and, furthermore, fine powders are likely to be formed since impact of particles becomes greater.

Furthermore, the rate of revolution of the rotor is preferably 20 to 1,000 rpm and, more preferably, 50 to 500 rpm. If the rate of revolution is smaller than 20 rpm, the thickness of the coating layer becomes nonhomogeneous. moreover, if the rate of revolution is greater than 1,000 rpm, there is a fear that the coating layer will be scraped off because of mutual collision of the coated particles and friction of the coated particles with the inner wall of the apparatus.

Drying is carried out continuously during the above spraying at an exhaust gas temperature of 25 to 70° C.; preferably, 30 to 60° C. The water content of the granulated product after drying is preferably 0 to 10%.

The first composition and the second composition are charged into a V-type mixer or the like, and an acid is further added and the components are mixed to form a solid preparation for dialysis. Examples of the above acid include acetic acid, hydrochloric acid, lactic acid and the like. Acetic acid is most preferably used among them. The above acid may include a solid acid such as citric acid, oxalic acid or the like, if necessary.

The order of mixing is preferably (1) mixing the first composition and the second composition, and further mixing the acid, or (2) mixing the first composition and the acid, and further mixing the second composition, for the purpose of preventing volatilization of the acid, and in order to react the acid and sodium acetate rapidly. When mixing is carried out in the above order (1), the acid is preferably added simultaneously when the first composition and the second composition are mixed, or is added just after mixing of the first composition and the second composition.

The solid preparation for dialysis of the present invention is used to form a dialysate by mixing it with a solid preparation containing sodium bicarbonate at a predetermined mixing ratio and subsequently dissolving the mixture into water. Moreover, after the above solid preparation for dialysis and sodium bicarbonate are respectively dissolved into water to make two aqueous solutions, the two solutions may be mixed to prepare a dialysate. Furthermore, after the above solid preparation for dialysis or sodium bicarbonate is dissolved into water to make an aqueous solution, the remaining preparation may be dissolved into the solution to prepare a dialysate.

When the solid preparation for dialysis of the present invention is dissolved together with sodium bicarbonate into water to prepare a dialysate, the dialysate has, for example, the following composition.

| | | |
|---|---|---|
| $Na^+$ | 120 to 150 | mEq/L |
| $K^+$ | 0.5 to 3 | mEq/L |
| $Ca^{2+}$ | 1.5 to 4.5 | mEq/L |
| $Mg^{2+}$ | 0.1 to 2.0 | mEq/L |
| $Cl^-$ | 90 to 135 | mEq/L |
| $CH_3COO^-$ | 5 to 15 | mEq/L |
| $HCO_3^-$ | 20 to 35 | mEq/L |
| Glucose | 0.5 to 2.5 | g/L |

The dialysate having the above composition preferably has a pH value of 7.2 to 7.4.

EXAMPLES

Hereinafter, the present invention is illustrated in more be detail by using examples. However, the present invention is not limited to these examples.

Example 1

Into 519.9 g of purified water, 36.6 g of potassium chloride, 25.0 g of magnesium chloride hexahydrate, 45.1 g of calcium chloride dihydrate and 110.8 g of sodium acetate anhydride were dissolved to prepare an aqueous solution. Into an agitating fluidized bed granulation apparatus (Multiplex MP-01, produced by Powrex Co., Ltd.), 1, 500 g of sodium chloride having an average particle diameter of 300 µm as core particles were charged. Under the conditions of an air feed temperature of 80° C., a rotor revolution rate of 300 rpm and an air feed flow rate of 40 m³/hr, the above aqueous solution was sprayed onto the core particles and dried at the same time to obtain granules of a first composition having an average particle diameter of 850 µm.

Separately, 77.8 g of sodium chloride, 10.4 g of potassium chloride, 7.1 g of magnesium chloride hexahydrate, 12.9 g of calcium chloride dihydrate and 31.6 g of sodium acetate anhydride were dissolved into 334.0 g of purified water to prepare an aqueous solution. Into an agitating fluidized bed granulation apparatus (Multiplex MP-01, produced by Powrex Co., Ltd.), 700.0 g of glucose having an average particle diameter of 180 µm and 349.7 g of sodium chloride as core particles were charged. Under the conditions of an air feed temperature of 60° C., rotor revolution rate of 200 rpm and an air feed flow rate of 40 m³/hr, the above aqueous solution was sprayed onto the core particles and dried at the same time to obtain granules of a second composition having an average particle diameter of 850 µm.

Next, 236.2 g of the granules of the first composition and 63.8 g of the granules of the second composition, which were cooled down to room temperature, were charged into a V-type mixer (S-3 type, produced by Tsutsui Rikagakukikai Co., Ltd.). Then, 5.64 g of glacial acetic acid were further added into the mixer and mixed homogeneously to obtain a solid preparation for dialysis having an average particle diameter of 850 µm.

Example 2

In the same manner as in Example 1, granules of a first composition and granules of a second composition each having an average particle diameter of 850 µm were obtained. Into a V-type mixer (S-3 type, produced by Tsutsui Rikagakukikai Co., Ltd.), 300.0 g of the granules of the first composition that was cooled down to room temperature were charged, and 6.44 g of glacial acetic acid were further added into the mixer, and the mixture was mixed. Subsequently, after the above mixture was taken out from inside of the mixer, 241.8 g of the mixture and 63.8 g of the granules of the second composition were charged into the V-type mixer, and mixing was carried out homogeneously to obtain a solid preparation for dialysis having an average particle diameter of 850 µm.

Comparative Example 1

Into an agitating mixer apparatus (vertical granulator VG-25, produced by Powrex Co., Ltd.), 3,000 g of sodium chloride, 73.3 g of potassium chloride, 49.9 g of magnesium chloride hexahydrate, 90.3 g of calcium chloride dihydrate, 221.6 g of sodium acetate anhydride and 491.2 g of glucose were charged. After mixing the mixture for ten minutes, 190 g of purified water were added to the mixture and the mixture was further mixed for 20 minutes. The composition thus obtained was placed into a fluidized dryer, and it was dried at 50° C. for one hour. The above composition, which was cooled down to room temperature, was charged into a V-type mixer (S-3 type, produced by Tsutsui Rikagakukikai Co., Ltd.), and 5.6 g of glacial acetic acid were further added into the mixer. Mixing was carried out homogeneously to obtain a solid preparation for dialysis having an average particle diameter of 350 μm.

Comparative Example 2

Into an agitating mixer apparatus (vertical granulator VG-25, produced by Powrex Co., Ltd.), 3,000 g of sodium chloride, 73.3 g of potassium chloride, 49.9 g of magnesium chloride hexahydrate, 90.3 g of calcium chloride dihydrate, 221.6 g of sodium acetate anhydride and 491.2 g of glucose were charged. After mixing the mixture for ten minutes, the mixture thus obtained was charged into a pulverizer (SW-1, produced by Powrex Co., Ltd.) to pulverize to an average particle diameter of 50 μm. Then, granulation was conducted by a roller compactor to obtain a composition having an average particle diameter of 500 μm. Subsequently, 300.0 g of the above composition were charged into a V-type mixer (S-3 type, produced by Tsutsui Rikagakukikai Co., Ltd.), and 5.6 g of glacial acetic acid were further added into the mixer. Mixing was carried out homogeneously to obtain a solid preparation for dialysis having an average particle diameter of 500 μm.

Test Results

With respect to the solid preparations for dialysis that were obtained in the above Examples 1 and 2 and Comparative Examples 1 and 2, content measurement of electrolytes, acetic acid, and glucose, evaluation of content homogeneity, and a stability test were carried out.

Content Measurement, Evaluation of Homogeneity

From each of the solid preparations for dialysis that were obtained in the above Examples 1 and 2 and Comparative Examples 1 and 2, 50 g of a sample were arbitrarily taken out six times, and the respective samples were dissolved into water to prepare 500 ml of an aqueous solution. The content of each component in the aqueous solution was measured. The proportion (%) of the average of the measured contents to the theoretical values and CV values (%) (coefficient of variation) are shown in Table 1.

In the content measurement, Na and K were measured with a flame photometer, Ca and Mg were measured by ion chromatography, acetic ion (AcO⁻) and citric acid were measured with HPLC-UV, Cl was measured by a silver nitrate titration method, and glucose was measured with a polarimeter.

other hand, the solid preparation for dialysis that is obtained by a wet granulation method in Comparative Example 1 and the solid preparation for dialysis that is obtained by a dry granulation method in Comparative Example 2 each had a nonhomogeneous content of glucose.

Stability Test

In a 100×100 mm aluminum wrapping material, 50 g of a sample of the respective solid preparations for dialysis that were obtained in the above Examples 1 and 2 and Comparative Examples 1 and 2 were enclosed. In the samples that were preserved (A) at 25° C., 60% RH for six months, or (B) at 40° C., 75% RH for three months, coloration of the solid preparations for dialysis in the wrapping material was measured with a color-difference meter (Z-300A, produced by Nippon Denshoku Co., Ltd.). The results are shown in Table 2.

TABLE 2

| | coloration just after production | coloration after preservation | |
|---|---|---|---|
| | | (A) | (B) |
| Example 1 | none | none | none |
| Example 2 | none | none | none |
| Comparative Example 1 | none | colored | colored |
| Comparative Example 2 | none | none | none |

As is apparent from Table 2, the solid preparation for dialysis of the present invention shows no coloration after a long-term preservation. On the other hand, the solid preparation for dialysis that is produced by the wet granulation method in Comparative Example 1 showed coloration after preservation.

Advantageous Effect of the Invention

According to the present invention, a solid preparation for dialysis that is excellent in content homogeneity can be provided by granulating separately a composition comprising electrolytes except for sodium bicarbonate and a composition comprising a sugar, and then mixing the compositions with an acid to produce the A preparation of a double preparation type sodium bicarbonate solid preparation. Moreover, a solid preparation for dialysis that shows no decomposition and coloration of glucose and is excellent in long-term preservation stability can be obtained.

What is claimed is:

1. A solid preparation for dialysis comprising a mixture of
   (a) a first composition which comprises core particles comprising particles of sodium chloride and a coating layer covering the core particles and containing one or more electrolytes selected from the group consisting of

TABLE 1

| | Example 1 | | Example 2 | | Comparative Example 1 | | Comparative Example 2 | |
|---|---|---|---|---|---|---|---|---|
| Component | Content (%) | CV value (%) | Content (%) | CV value (%) | Content (%) | CV value (%) | Content (%) | CV value (%) |
| Na⁺ | 99.4 | 0.4 | 99.6 | 0.3 | 97.4 | 4.3 | 98.6 | 3.9 |
| K⁺ | 98.9 | 0.6 | 99.0 | 0.6 | 95.3 | 3.2 | 95.1 | 4.0 |
| Ca²⁺ | 99.8 | 0.8 | 100.5 | 0.8 | 102.8 | 3.1 | 99.3 | 2.9 |
| Mg²⁺ | 100.3 | 1.1 | 101.0 | 0.8 | 98.0 | 2.9 | 97.9 | 2.5 |
| AcO⁻ | 99.5 | 0.5 | 99.6 | 0.6 | 97.2 | 3.0 | 97.7 | 3.2 |
| Cl⁻ | 100.2 | 0.2 | 100.6 | 0.3 | 98.0 | 4.1 | 99.3 | 2.2 |
| Glucose | 99.0 | 1.1 | 99.1 | 1.0 | 131.5 | 20.8 | 110.9 | 12.9 |

Content (%) = (average of the measured contents) / (the theoretical value) × 100 (%)

As is apparent from Table 1, in the solid preparation for dialysis of the present invention the averages of the respective contents are close to the theoretical values, CV value is also small, and content homogeneity is excellent. On the calcium chloride, magnesium chloride, potassium chloride and sodium acetate, (b) particles of a second composition which comprises core particles comprising particles of a sugar and a coating layer covering the core particles and containing one or more electrolytes selected from the group consisting of sodium chloride, calcium chloride, magnesium chloride, potassium chloride and sodium acetate, and (c) an acid.

2. The solid preparation for dialysis as claimed in claim 1, wherein the acid is acetic acid, hydrochloric acid or lactic acid.

3. The solid preparation for dialysis as claimed in claim 1, wherein the first composition is granulated into granules having an average particle diameter of 300 to 1,700 μm and the second composition is granulated into granules having an average particle diameter of 300 to 1,700 μm.

4. A sodium bicarbonate solid preparation for dialysis comprising the solid preparation for dialysis claimed in claim 1 and a solid preparation containing sodium bicarbonate.

5. The solid preparation for dialysis as claimed in claim 1, wherein the core particles of the first composition include up to 15% by weight, based on the weight of the core particles, of particles of an electrolyte selected from the group consisting of magnesium chloride, calcium chloride, potassium chloride and sodium acetate.

6. The solid preparation for dialysis as claimed in claim 1, wherein the core particles of the second composition include up to 50% by weight, based on the weight of the core particles, of particles of an electrolyte selected from the group consisting of sodium chloride, magnesium chloride, calcium chloride, potassium chloride and sodium acetate.

7. The solid preparation for dialysis as claimed in claim 1, wherein the coating layer of the first composition further comprises up to 50% by weight, based on the weight of the coating layer, of sodium chloride.

8. The solid preparation for dialysis as claimed in claim 1, wherein the coating layer of the second composition further comprises up to 50% by weight, based on the weight of the coating layer, of glucose.

\* \* \* \* \*

UNITED STATES PATENT AND TRADEMARK OFFICE
CERTIFICATE OF CORRECTION

PATENT NO.    : 6,464,977 B2
DATED         : October 15, 2002
INVENTOR(S)   : Toshiya Kai et al.

It is certified that error appears in the above-identified patent and that said Letters Patent is hereby corrected as shown below:

<u>Title page,</u>
Item [75], second inventor's address "Osaki" should read -- Osaka --.

Signed and Sealed this

Fourth Day of February, 2003

JAMES E. ROGAN
*Director of the United States Patent and Trademark Office*